United States Patent [19]

Farge et al.

[11] 4,269,842

[45] May 26, 1981

[54] METHOD FOR TREATING RHINOVIRAL COMPLAINTS

[75] Inventors: Daniel Farge, Thiais; Alain Jossin, St-Cloud; Gerard Ponsinet, Sucy-en-Brie; Daniel Reisdorf, Thiais, all of France

[73] Assignee: Rhone-Poulenc Industries, Paris, France

[21] Appl. No.: 100,524

[22] Filed: Dec. 5, 1979

[51] Int. Cl.³ .............................................. A61K 31/47
[52] U.S. Cl. ...................................................... 424/258
[58] Field of Search ......................................... 424/258

[56] References Cited

U.S. PATENT DOCUMENTS 4,064,247  12/1977  Farge et al. ..................... 424/258
4,153,698  5/1979  Farge et al. ..................... 424/258

Primary Examiner—Jerome D. Goldberg
Attorney, Agent, or Firm—Stevens, Davis, Miller & Mosher

[57] ABSTRACT

Rhinoviral complaints are treated by administering a product of the general formula:

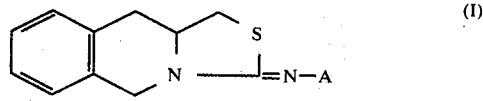

in the (S) form, in which formula A is pyrid-3-yl which is unsubstituted or substituted in the 2-position by chlorine, fluorine or methoxy, isoquinol-5-yl, or 3-methyl-isoquinol-5-yl, or one of its pharmaceutically acceptable salts.

6 Claims, No Drawings

METHOD FOR TREATING RHINOVIRAL COMPLAINTS

DESCRIPTION

The present invention relates to the treatment of rhinoviral complaints.

According to the present invention a method for treating rhinoviral complaints comprises administering to a mammal subject thereto, i.e. suffering from an infection by a rhinovirus or liable to such an infection, an effective amount of a compound of the formula:

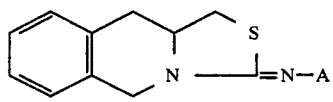 (I)

in the S form, in which A represents pyrid-3-yl, 2-chloro-pyrid-3-yl, 2-fluoro-pyrid-3-yl, 2-methoxypyrid-3-yl, isoquinol-5-yl, or 3-methylisoquinol-5-yl, or of a pharmaceutically acceptable salt of such a compound.

The compounds of the formula (I) and their preparation are described in U.S. Pat. Nos. 4,064,247 and 4,153,698 and in French Pat. No. 2,320,098. According to these patents, the compounds possess analgesic and anti-pyretic activity and, in certain cases, anti-inflammatory activity.

Rhinoviruses belong to the group of the picornaviruses, which comprise about one hundred different antigenic species; they are responsible for about 70% of infectious colds in the human population.

The compounds of the formula (I) and their salts possess valuable anti-viral activity against rhinoviruses. Of particular interest are those compounds of general formula I having the S form as such or in admixture with a substantial amount of the R form.

The type 1 A (R 2060 strain) and type 1 B (R 1112 strain) human rhinoviruses have the property of forming foci of necrosis (cytopathogenic effect) on single-layer cell cultures. The compounds of the formula (I), which prevent the formation of these foci, have been selected as active substances.

This activity was demonstrated in the following manner: cell cultures of human fibroblasts (MCR-5), in a passive medium (1.7 cc) composed of Eagle's Basal Medium in Earle's saline solution to which 2% of calf serum, 2.5% of a 5.5% aqueous solution of $NaHCO_3$, and 100 $\mu g/cm^3$ of a mixture (50/50 by weight) of penicillin and streptomycin have been added, receive 0.1 $cm^3$ of decreasing concentrations (between 2,500 and 1.2 $\mu g/cm^3$) of the solution or suspension of the compounds under test (solution in distilled water or in dimethylsulphoxide and dilution in isotonic phosphate buffer at pH=7.4; final concentration of the dimethylsulphoxide=1.25% in the cultures). The maximum non-cytotoxic concentration, that is to say the concentration which does not cause any adverse morphological change in the cells, a concentration which is twice as high being cytotoxic, is determined.

Decreasing concentrations of the same solution or suspension of the compound under test are added to fresh identical cell cultures, the highest concentration being the maximum non-cytotoxic concentration. About one hour after the compounds have been added, the cultures are inoculated with 0.2 $cm^3$ of a suitably diluted suspension of virus (in isotonic phosphate buffer), which is capable of destroying about 75% of cells (cytopathogenic effect). 5 Control cultures (without test compound) are also inoculated. All the cultures are then incubated at 37° C. in a "roller" tissue culture apparatus at the same time as 2 control cultures (without test compound or virus) which have received 0.2 $cm^3$ of isotonic phosphate buffer. 3–4 Days after the start of the experiment, the cytopathogenic effect of the virus is examined under a microscope. The active compounds are those which have prevented the appearance of the cytopathogenic effect, and those which have inhibited it by at least 50% are considered to be partially active.

The results obtained are summarised in the Table below:

| Compound No. | —A | Maximum cytotoxic concentration $\mu g/cm^3$ | Minimum inhibitory concentration | |
|---|---|---|---|---|
| | | | Rhinovirus type 1 A | Rhinovirus type 1 B |
| 1 | pyrid-3-yl | more than 30 | 15 | 0.15 |
| 2 | 2-Cl-pyrid-3-yl | 15 | partially active at 15 | 0.016 |
| 3 | 2-F-pyrid-3-yl | 15 | 15 | 0.016 |
| 4 | 2-OCH$_3$-pyrid-3-yl | 15 | partially active at 15 | 1.5 |
| 5 | isoquinol-5-yl | more than 60 | 0.7 | 0.7 |
| 6 | 3-CH$_3$-isoquinol-5-yl | 30 | 1.5 | 1.5 |

The compounds of the formula (I) can be employed in the form of pharmaceutical compositions, in which the compound of formula I, or a pharmaceutically acceptable salt thereof, is associated with one or more pharmaceutically acceptable diluents, including coatings, or adjuvants. Such compositions may be in a form suitable for intranasal or oral administration. These compositions are particularly indicated for the treatment of viral complaints in the respiratory tract.

In human therapy, the doses to be used depend on the desired effect, the method of administration and the duration of the treatment; for an adult, they can generally be between 0.1 and 2 g of active product per day, administered orally; they can reach 100 mg per day using nasal administration (drops or sprays).

Tablets, pills, powders, sugar-coated pills or granules can be used as solid compositions for oral administration. In these compositions, the active product is mixed with one or more inert diluents such as sucrose, lactose or starch. These compositions can also comprise substances other than diluents, e.g. a lubricant such as magnesium stearate.

Solutions, suspensions, syrups, elixirs containing inert diluents such as water or paraffin oil, and pharmaceutically acceptable emulsions can be used as liquid compositions for oral administration. These compositions can also comprise substances other than diluents, e.g. wetting agents, sweetening agents or flavourings.

The compositions, according to the invention, for intranasal administration can be non-aqueous sterile solutions, or aqueous or non-aqueous suspensions or emulsions. Propylene glycol, polyethylene glycol, vegetable oils, in particular olive oil, sweet-almond oil or coconut oil, and organic esters, e.g. ethyl oleate, can be employed as the solvent or vehicle.

These compositions can also contain adjuvants, in particular wetting agents, emulsifiers and dispersing agents (e.g. soya lecithin). Sterilisation can be carried out in several ways, e.g. using a bacteriological filter, by incorporating sterilising agents into the composition, by irradiation, by heating or by adding a preservative. The compositions can also be prepared in the form of sterile solid compositions which can be dispersed or dissolved, at the time of use, in sterile water or any other suitable sterile medium.

The following Example illustrates a composition according to the invention.

EXAMPLE

Tablets (0.400 g) each containing an 0.200 g dose of active product and having the following composition are prepared:

| | |
|---|---|
| (S)-3-(3-methylisoquinol-5-yl)-imino-1,5,10,10a-tetrahydrothiazolo[3,4-b]isoquinoline | 0.200 g |
| corn starch | 0.137 g |
| dicalcium phosphate | 0.040 g |
| sodium carboxymethyl starch | 0.015 g |
| magnesium stearate | 0.008 g |

The active principle, the dicalcium phosphate and about 90% of the starch are mixed and then passed through a sieve (mesh size: 0.5 mm). The product is converted into a paste using a 10% starch paste made from the remaining 10% of starch, the resulting paste is converted into granules by passing it through a sieve (mesh size: 0.8 mm) and the granules are dried in an oven at about 50° C. The sodium carboxymethyl starch and the magnesium stearate are then added and the mixture is compressed.

The preparation of Compounds Nos. 1 and 5 is described in U.S. Pat. No. 4,064,247. The preparation of Compound No. 6 is described in U.S. Pat. No. 4,153,698.

Compounds Nos. 2, 3 and 4 are prepared as described in, or by applying the methods described in, French patent published under number 2,320,098, in accordance with the Examples below:

EXAMPLE 1

Compound 3 is prepared by proceeding as follows:
(S)-3-Methylthio-1,5,10,10a-tetrahydrothiazolo-[3,4-b]isoquinolinium iodide (40 g) is added to a solution of 3-amino-2-fluoropyridine (12.3 g) in anhydrous pyridine (540 cm$^3$). After 20 hours at a temperature of about 20° C., the solid has totally dissolved. The solution is concentrated to dryness under reduced pressure (25 mm Hg) without exceeding 50° C.

The residue is dissolved in a mixture consisting of 2 N sodium hydroxide solution (200 cm$^3$) and methylene chloride (200 cm$^3$). The organic phase is decanted and the aqueous phase is then extracted with methylene chloride (3×200 cm$^3$). The combined organic extracts are dried over sodium sulphate and filtered and the filtrate is concentrated to dryness under reduced pressure (25 mm Hg). The residue is taken up in isopropyl ether (200 cm$^3$) and the insoluble crystalline material is then filtered off. The crystals thus obtained are dissolved in boiling ethanol (450 cm$^3$). After filtering and cooling the filtrate to 5° C., the crystals are filtered off and washed with ethanol (30 cm$^3$).

After a second recrystallization from ethanol (500 cm$^3$), (S)-3-[(2-fluoropyrid-3-yl)-imino]-1,5,10,10a-tetrahydrothiazolo[3,4-b]-isoquinoline (22 g) is obtained in the form of white crystals melting at 151°–152° C.
$[\alpha]_D^{20} = -246 \pm 3°$ (c=1.2, chloroform).

3-Amino-2-fluoropyridine was prepared according to G. C. FINGER et al., J. Org. Chem., 27, 3,965 (1962).

(S)-3-Methylthio-1,5,10,10a-tetrahydrothiazolo[3,4-b]isoquinolinium iodide was prepared in accordance with the method described in U.S. Pat. No. 4,064,247.

EXAMPLE 2

Compound 2 is prepared by proceeding as follows:
By following the procedure of Example 1, but using (S)-3-methylthio-1,5,10,10a-tetrahydrothiazolo[3,4-b]isoquinolinium iodide (36.3 g) and 3-amino-2-chloropyridine (26.0 g) as the starting materials, (S)-3-[(2-chloropyrid-3-yl)-imino]-1,5,10,10a-tetrahydrothiazolo[3,4-b]isoquinoline (11.2 g), which melts at 178° C. after recrystallization from ethanol, is obtained.
$[\alpha]_D^{20} = -224 \pm 2°$ (c=2; chloroform).

EXAMPLE 3

Compound 4 is prepared by proceeding as follows:
A 1.6% (weight/volume) solution of diazomethane in ether (150 cm$^3$) is added to a solution of (S)-3-[(2-hydroxypyrid-3-yl)-imino]-1,5,10,10a-tetrahydrothiazolo[3,4-b]isoquinoline (11.8 g) in dimethylformamide (600 cm$^3$). After 3 days at a temperature of the order of 20° C., the ether is evaporated under reduced pressure (40 mm Hg) at 40° C. and a 1.6% solution of diazomethane in ether (175 cm$^3$) is then added. This operation is repeated after 3 days and the reaction is allowed to proceed for 3 days. The mixture is concentrated to dryness under reduced pressure (20 mm Hg at 80° C. and then 1 mm Hg at 70° C.). The residue is chromatographed on a column of silica (220 g) (diameter of the column: 3 cm), elution is carried out with methylene chloride and fractions (300 cm$^3$) are collected. Fractions 2 to 5 are combined and evaporated to dryness. The resulting residue is recrystallized from acetonitrile, and (S)-3-[(2-methoxypyrid-3-yl)-imino]-1,5,10,10a-tetrahydrothiazolo[3,4-b]isoquinoline (3.4 g) is thus obtained in the form of white crystals melting at 142° C.
$[\alpha]_D^{20} = -215 \pm 3°$ (c=1; chloroform).

(S)-3-[(2-Hydroxypyrid-3-yl)-imino]-1,5,10,10a-tetrahydrothiazolo[3,4-b]isoquinoline can be prepared in the following manner. A solution of sodium nitrite (3.8 g) in water (10 cm$^3$) is added dropwise to a solution of (S)-3-[(2-aminopyrid-3-yl)-imino]-1,5,10,10a-tetrahydrothiazolo[3,4-b]isoquinoline (16.7 g) in a mixture of water (20 cm$^3$) and sulphuric acid (d=1.8; 92% by weight) (50 cm$^3$), the reaction mixture being kept at a temperature of the order of 2° C. The resulting brown solution is poured into a mixture, heated to 145° C., of water (30 cm$^3$) and sulphuric acid (d=1.83) (80 cm$^3$), and this temperature is maintained until the evolution of gas has ended. The solution, cooled to 40° C., is poured onto crushed ice (500 g) and then neutralized with ammonia solution (d=0.90; 15 N). A brown solid is formed which is filtered off and then dissolved in boiling methylene chloride (200 cm³). The solution is cooled to 5° C. and the crystals which have appeared are filtered off.

(S)-3-[(2-Hydroxypyrid-3-yl)-imino]-1,5,10,10a-tetrahydrothiazolo[3,4-b]isoquinoline (10.7 g) is thus obtained in the form of light grey crystals melting at 225°–226° C.

$[\alpha]_D^{20} = -265 \pm 3°$ (c=1; chloroform).

(S)-3-[(2-Aminopyrid-3-yl)-imino]-1,5,10,10a-tetrahydrothizolo[3,4-b]isoquinoline can be prepared in the following manner:

(S)-3-Methylthio-1,5,10,10a-tetrahydrothiazolo[3,4-b]isoquinoline iodide (123.5 g) is added to a solution of 2,3-diaminopyridine (44.5 g) in pyridine (1,200 cm³). After 3 days at a temperature of the order of 20° C., the suspension is concentrated to dryness under reduced pressure (20 mm Hg) at 70° C. The residue is dissolved in a mixture of 2 N sodium hydroxide solution (250 cm³) and methylene chloride (1,000 cm³). The organic phase is decanted, washed with water (3×250 cm³), dried over magnesium sulphate and then concentrated to dryness under reduced pressure (25 mm Hg) at 40° C. The evaporation residue is recrystallized from isopropanol (1,300 cm³). After drying at 60° C. under reduced pressure (0.1 mm Hg), (S)-3-[(2-aminopyrid-3-yl)-imino]-1,5,10,10a-tetrahydrothiazolo[3,4-b]isoquinoline (52.0 g), which melts at 196° C., is obtained.

$[\alpha]_D^{20} = -166 \pm 2°$ (c=1; chloroform).

We claim:

1. A method for treating rhinoviral complaints, which comprises administering to a mammal in need of said treatment an effective anti-rhinoviral amount of a compound of the formula:

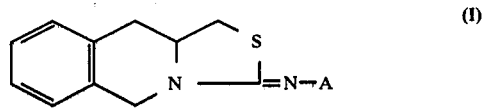

in the S form, in which A is pyrid-3-yl, 2-chloropyrid-3-yl, 2-fluoro-pyrid-3-yl, 2-methoxy-pyrid-3-yl, isoquinol-5-yl, or 3-methylisoquinol-5-yl or a pharmaceutically acceptable salt thereof.

2. A method according to claim 1, wherein the administration is carried out orally.

3. A method according to claim 1, wherein the administration is carried out nasally.

4. A method according to claim 1, wherein (S)-3-(3-methylisoquinol-5-yl)-imino-1,5,10,10a-tetrahydrothiazolo[3,4-b]isoquinoline or a pharmaceutically acceptable salts thereof is administered.

5. A method according to claim 1, wherein (S)-3-(pyrid-3-ylimino)-1,5,10,10a-tetrahydrothiazolo[3,4-b]isoquinoline or a pharmaceutically acceptable salts thereof is administered.

6. A method according to claim 1, wherein (S)-3-(isoquinol-5-yl)-imino-1,5,10,10a-tetrahydrothiazolo[3,4-b]isoquinoline or a pharmaceutically acceptable salts thereof is administered.

* * * * *